US011782113B2

(12) United States Patent
Prchkovska et al.

(10) Patent No.: US 11,782,113 B2
(45) Date of Patent: *Oct. 10, 2023

(54) FIBER TRACKING AND SEGMENTATION

(71) Applicant: Mint Labs Inc., Boston, MA (US)

(72) Inventors: Vesna Prchkovska, Barcelona (ES); Paulo Reis Rodrigues, Barcelona (ES); Matthew Rowe, Barcelona (ES)

(73) Assignee: Mint Labs Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/739,430

(22) Filed: May 9, 2022

(65) Prior Publication Data

US 2022/0335618 A1    Oct. 20, 2022

Related U.S. Application Data

(63) Continuation of application No. 16/652,021, filed as application No. PCT/US2018/054029 on Oct. 2, 2018, now Pat. No. 11,328,426.

(Continued)

(51) Int. Cl.
*G06K 9/00* (2022.01)
*G01R 33/563* (2006.01)
*G06T 7/143* (2017.01)
*G06T 7/11* (2017.01)
*G16H 30/40* (2018.01)
*A61B 5/00* (2006.01)
(Continued)

(52) U.S. Cl.
CPC ...... *G01R 33/56341* (2013.01); *A61B 5/0013* (2013.01); *A61B 5/0022* (2013.01); *A61B 5/0042* (2013.01); *A61B 5/055* (2013.01); *G01R 33/5608* (2013.01); *G06T 7/0012* (2013.01); *G06T 7/11* (2017.01); *G06T 7/143* (2017.01); *G16H 30/40* (2018.01);
(Continued)

(58) Field of Classification Search
CPC . G06F 30/00; G06F 30/20; G06F 9/48; G06F 9/4843; G06F 9/4881; G06F 9/50; G06F 9/52; G06N 3/08; G06N 20/00; G06N 3/0454; G06N 3/04; G06N 5/046; G06N 3/0445; G06N 7/005; G06N 20/10; G06N 20/20; G06N 3/02; G06N 3/049; G06N 3/063; G06N 3/0675; G06N 5/003; G06N 5/04

See application file for complete search history.

(56) References Cited

U.S. PATENT DOCUMENTS 11,328,426 B2 * 5/2022 Prchkovska ........... A61B 5/743
2006/0233430 A1 10/2006 Kimura
(Continued)

OTHER PUBLICATIONS

Chen, RACTGRAPHCNN: Anatomically Informed Graph CNN for Classification Using Diffusion MRI Tractography, 2023, arXiv (Year: 2023).*
(Continued)

*Primary Examiner* — Alex Kok S Liew
(74) *Attorney, Agent, or Firm* — Foley & Lardner LLP

(57) ABSTRACT

The present solution can segment tracts by performing two-pass tractography. The system can first perform deterministic tractography and then probabilistic tractography. The system can use the result from the deterministic tractography to update and refine initial identified regions of interest. The refined regions of interest can be used to filter and select streamlines identified through the probabilistic tractography.

20 Claims, 11 Drawing Sheets

Related U.S. Application Data

(60) Provisional application No. 62/567,646, filed on Oct. 3, 2017.

(51) Int. Cl.
*A61B 5/055* (2006.01)
*G01R 33/56* (2006.01)
*G06T 7/00* (2017.01)
*G16H 40/63* (2018.01)

(52) U.S. Cl.
CPC ............... *A61B 2576/026* (2013.01); *G06T 2207/10092* (2013.01); *G06T 2207/30016* (2013.01); *G16H 40/63* (2018.01)

(56) References Cited

U.S. PATENT DOCUMENTS

| | | | |
|---|---|---|---|
| 2007/0092120 A1* | 4/2007 | Guo | G06T 7/149 382/128 |
| 2010/0004527 A1* | 1/2010 | Dale | G01R 33/56341 600/410 |
| 2013/0223714 A1 | 8/2013 | Lipton et al. | |
| 2013/0278257 A1 | 10/2013 | Boada et al. | |
| 2014/0294270 A1* | 10/2014 | Schneider | A61B 5/055 382/131 |
| 2017/0052241 A1 | 2/2017 | Cetingul et al. | |

OTHER PUBLICATIONS

Foreign Action other than Search Report on PCT PCT/US2018/054029 dated Apr. 17, 2020.
International Preliminary Report on Patentability; dated Apr. 17, 2020; 7pgs.
Non-Final Office Action on U.S. Appl. No. 17/739,430 dated Feb. 16, 2023.
U.S. Notice of Allowance on U.S. Appl. No. 16/652,021 dated Jan. 10, 2022.
Written Opinion and International Search Report dated Nov. 20, 2018; 8 pgs.

* cited by examiner

900

Right inferior longitudinal fasciculus (ILF)

Left superior longitudinal fasciculus (SLF)

Right superior longitudinal fasciculus (SLF)

Left cortico-spinal tract (CST)

FIBER TRACKING AND SEGMENTATION

CROSS-REFERENCE TO RELATED APPLICATION

The present application is a continuation and claims priority to and the benefit of U.S. Non-Provisional patent application Ser. No. 16/652,021, titled "FIBER TRACKING AND SEGMENTATION," filed Mar. 27, 2020, which is a national phase of Application Number No. PCT/US2018/054029, titled "FIBER TRACKING AND SEGMENTATION," filed Oct. 2, 2018, which claims priority to and the benefit of U.S. Provisional Patent Application No. 62/567,646, titled "FIBER TRACKING AND SEGMENTATION," filed Oct. 3, 2017. The contents of the foregoing applications are incorporated herein by reference in their entireties.

BACKGROUND OF THE DISCLOSURE

Diffusion-weighted Mill (DW-MRI) is a magnetic resonance imaging technique that can enable the measurement of the directional diffusion of water molecules embedded in tissues within the body. The directional dispersion of water molecules reveals structural features of the tissue. Like other Mill techniques, it is safe, non-invasive, and routine to use on a live patient.

This capability of the DW-MRI technique is particularly powerful when used to examine white matter in the brain, which is made up of the fibrous bundles of axons which connect neurons in different parts of the brain. The way the brain is connected by these fibers defines how the brain functions.

The fibers traversing the brain are organized into large collections or bundles, often referred to as "fascicles" which converge to create well-defined structures which connect particular parts of the brain with particular functions. There are, for example, white matter fascicles that can be used in brain functions such as language, vision, or hearing.

SUMMARY OF THE DISCLOSURE

White matter structures in the brain can be manually delineated. A person with the appropriate technical and anatomical knowledge can use an image viewer to manually define virtual regions of interest drawn upon a visualization of the MM scan in different 2D planes (e.g., axial, sagittal, and coronal). However, manual delineation can result in inter-operator variances and the process cannot be accurately reproduced by automated tools. This presents several problems.

To perform a manual delineation, the operator must have sufficient understanding of both the white matter anatomy and the technical details and limitations of the tractography technique to successfully delineate the various structures. This can result in a process that is extremely time consuming. Additionally, the use of human operators causes significant variability in inter-operator results.

The present solution described herein can overcome these problems. The system can automatically give identical results on the same dataset without the intervention of a human operator.

The system can segment tracts by performing two-pass tractography. The system can first perform deterministic tractography and then probabilistic tractography. Using deterministic or probabilistic tractography in isolation can result in the over or under estimation of fascicles. However, combining deterministic and probabilistic tractography in a two-pass method, as described herein, can enable the location and boundaries of the fascicles are adequately covered with less likelihood of over or underestimation. For example, the system can remind broadly defined ROIs using deterministic tractography before applying probabilistic tractography to estimate the larger spatial extent of the fascicle.

The system can also perform tractography based on constrained spherical deconvolution modeling of diffusion-weighted MRI data. Constrained spherical deconvolution can robustly define complicated structures at the local, voxel-wise scale, such as crossing fibers.

According to at least one aspect of the disclosure, a data processing system can include one or more processors to segment neurological tracts. The data processing system can include a segmentation engine. The segmentation engine can receive image data including an anatomical image and a diffusion-weighted (DW) image. The segmentation engine can determine a region of interest in the anatomical image. The region of interest can include a first plurality of voxels. The segmentation engine can generate a first plurality of streamlines indicating a fiber tract in the DW image. The segmentation engine can determine an updated region of interest. The updated region of interest can include a portion of the first plurality of voxels. The at least one of the first plurality of streamlines can pass through each voxel of the portion of the first plurality of voxels. The segmentation engine can generate a second plurality of streamlines. Each of the second plurality of streamlines can indicate a candidate fiber tract. The segmentation engine can select a portion of the second plurality of streamlines. Each of the portions of the second plurality of streamlines can pass through the updated region of interest. The segmentation engine can generate a tract image including the portion of the second plurality of streamlines. Each of the portions of the second plurality of streamlines pass through the updated region of interest.

In some implementations, the segmentation engine generates the plurality of streamlines indicating the fiber tract with deterministic tractography. The segmentation engine can generate the second plurality of streamlines with probabilistic tractography. The segmentation engine can map the region of interest from a template to the anatomical image. The template can include a Montreal Neurological Institute (MNI) template image. The segmentation engine can warp the template to the anatomical image with a symmetric, invertible warp.

In some implementations, the segmentation engine can generate the first plurality of streamlines using constrained spherical deconvolution. The tract image can include the portion of the second plurality of streamlines aligned with the anatomical image. The anatomical image can be an MRI image.

In some implementations, the segmentation engine can determine a second region of interest in the anatomical image. The second region of interest can include a second plurality of voxels. The segmentation engine can determine a second updated region of interest. The second updated region of interest can include a portion of the second plurality of voxels. At least one of the first plurality of streamlines passes through each voxel of the portion of the second plurality of voxels. The segmentation engine can select the second plurality of streamlines. Each of the portions of the second plurality of streamlines pass through the second updated region of interest.

According to at least one aspect of the disclosure, a method to segment neurological tracts can include receiving, by a segmentation engine, image data that can include an anatomical image and a DW image. The method can include determining, by the segmentation engine, a region of interest in the anatomical image. The region of interest can include a first plurality of voxels. The method can include generating, by the segmentation engine, a first plurality of streamlines indicating a fiber tract in the DW image. The method can include determining, by the segmentation engine, an updated region of interest. The updated region of interest can include a portion of the first plurality of voxels. At least one of the first plurality of streamlines passes through each voxel of the portion of the first plurality of voxels. The method can include generating, by the segmentation engine, a second plurality of streamlines. Each of the second plurality of streamlines can represent a candidate fiber tract. The method can include selecting, by the segmentation engine, a portion of the second plurality of streamlines. Each of the portions of the second plurality of streamlines can pass through the updated region of interest. The method can include generating, by the segmentation engine, a tract image comprising the portion of the second plurality of streamlines, wherein each of the portions of the second plurality of streamlines pass through the updated region of interest.

In some implementations, the method can include generating the plurality of streamlines indicating the fiber tract with deterministic tractography. The method can include generating the second plurality of streamlines with probabilistic tractography. The method can include mapping the region of interest from a template to the anatomical image. The template comprises a Montreal Neurological Institute (MNI) template image. The method can include warping the template to the anatomical image with a symmetric, invertible warp.

In some implementations, the method can include generating the first plurality of streamlines using constrained spherical deconvolution. The tract image can include the portion of the second plurality of streamlines aligned with the anatomical image. The anatomical image can be an MRI image.

In some implementations, the method can include determining, by the segmentation engine, a second region of interest in the anatomical image. The second region of interest can include a second plurality of voxels. The method can include determining, by the segmentation engine, a second updated region of interest. The second updated region of interest can include a portion of the second plurality of voxels. At least one of the first plurality of streamlines can pass through each voxel of the portion of the second plurality of voxels. The method can include selecting, by the segmentation engine, the second plurality of streamlines. Each of the portion of the second plurality of streamlines can pass through the second updated region of interest.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

Figure 1:
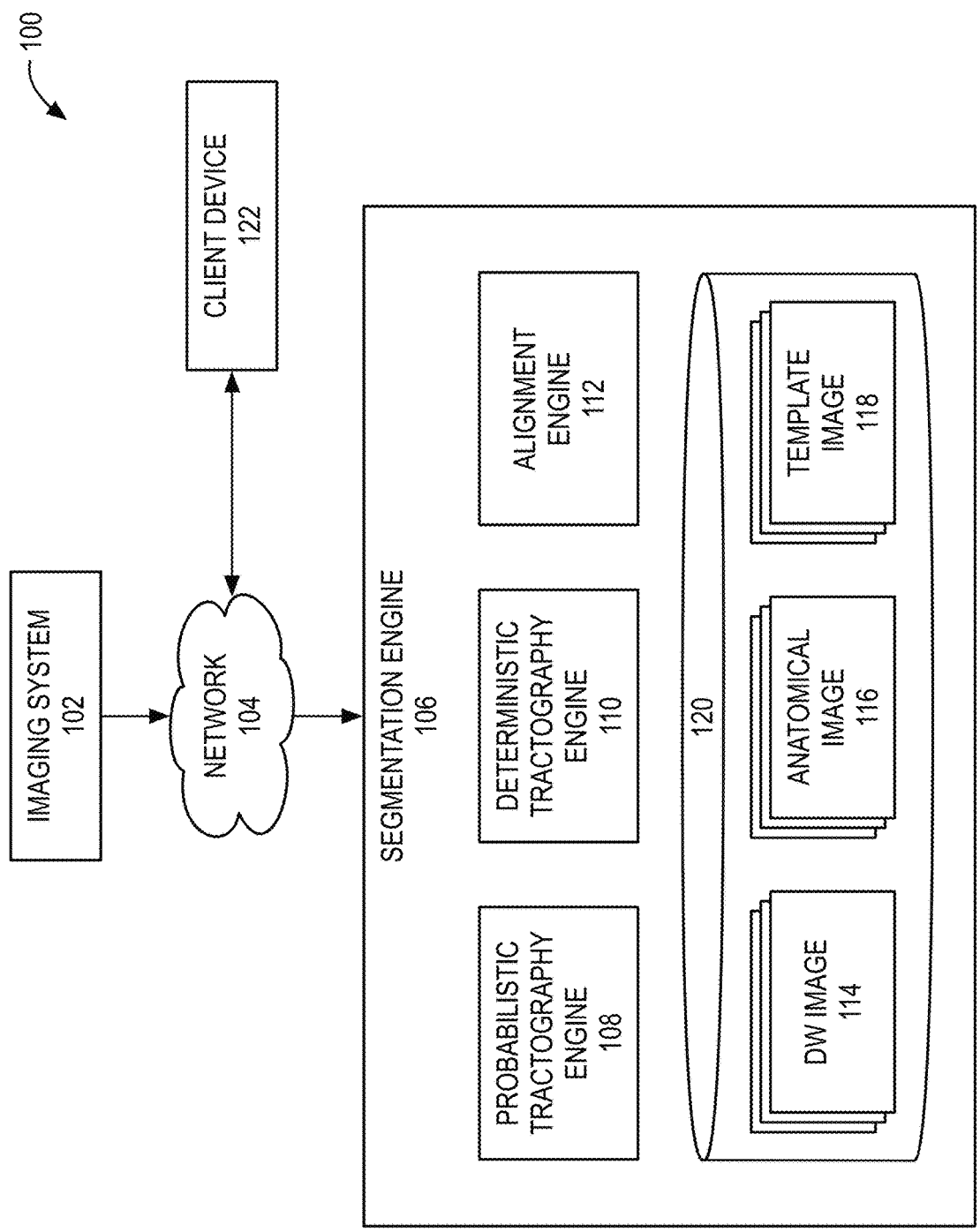
FIG. 1 illustrates an example system to generate tract segmentations from neuroimages.

The various concepts introduced above and discussed in greater detail below may be implemented in any of numerous ways, as the described concepts are not limited to any particular manner of implementation. Examples of specific implementations and applications are provided primarily for illustrative purposes.

The present solution can provide a medical image processing pipeline that can use different sequence types of magnetic resonance images (MM) (e.g., a T1 weighted "anatomical scan" and a diffusion-weighted MR image (DW-MRI) to segment white matter structures in the brain. The present system can determine scalar metrics derived from the diffusion-weighted images which can be linked to tissue integrity or reflect changes in tissue structure. The system can be used to study fascicle-specific structural changes induced by disease or aging.

The present solution can segment tracts by performing two-pass tractography. The system can first perform deterministic tractography and then probabilistic tractography. The system can use the result from the deterministic tractography to update and refine initial identified virtual waypoints. The refined regions of interest can be used to filter and select streamlines identified through the probabilistic tractography.

The system can use as input, T1 weighted images and a multi-direction diffusion-weighted images (e.g., diffusion tensor imaging (DTI) or high angular resolution diffusion-weighted image (HARDI)). Using regions of interest (ROIs) from template images, the system can warp the ROIs into the subject's images.

The system can use diffusion tensor models or constrained spherical deconvolution to determine the fiber direction distribution in each voxel. The system can then follow these fiber directions from a seed voxel to estimate white matter fiber trajectories between brain structures. The system can use a two-pass tractography method whereby the broad ROIs defined in the templates (e.g., in the template space) are propagated into the subject's images (e.g., into the subject space). The system can identify the intersections between deterministically determined streamlines to define more anatomically meaningful ROIs for the subject. For example, the system can refine the ROIs by maintaining only the portions of the original ROIs where the streamlines intersect the original ROIs. The refined ROIs can be used as waypoints for the filtering of the second tractography pass, which uses probabilistic streamlines to create a probabilistic map of voxel-fiber membership. For example, the system can assign a probability for each voxel to belong to the relevant fascicle. The system can use weighted statistics to calculate the mean scalar diffusion metrics for each fascicle, such that voxels for which there is significant confidence of fascicle membership have more influence on the summary statistic than other voxels (e.g. near the boundaries of the fascicle) for which there is less confidence of fascicle membership. For example, the probabilistic map of voxel-fiber membership can include a number for each voxel which is proportional to the number of streamlines crossing the respective voxel. In a voxel that is intersected by many streamlines estimated to be members of the candidate fascicle, the number for the voxel is high, whereas, in any voxel intersected by very few streamlines estimated to be members of the candidate fascicle this number will be low. In some implementations, the voxel can be retained as a member of the fascicle if the number is above a predetermined threshold.

For each fascicle, the system can determine a mean value for different scalar diffusion-weighted imaging metrics across the extent of the fascicle. The contributions of each voxel can be weighted by the fiber membership probability value in that voxel. The scalar metrics extracted can include the fractional anisotropy (FA), the mean diffusivity (MD), the radial diffusivity (RD), the coefficient of sphericity (Cs), the coefficient of planarity (Cp), and the coefficient of linearity (Cl). These metrics have the potential to inform on tissue changes reflecting pathology. For example, an increase in radial diffusivity can indicate degradation in myelin integrity, while a decrease in axial diffusivity can indicate acute axonal damage.

In some implementations, the system can be a cloud-based system, which enables management of the input data and results from the tool. The system can be accessed at a client device through a web-browser. Results of the tool can be visualized easily using the features of the platform, making the tool accessible to technically naive users from clinical centers.

FIG. 1 illustrates an example system 100 to generate tract segmentations from neuroimages. The system 100 includes an imaging system 102. The imaging system 102 can communicate with a segmentation engine 106 locally or over a network 104. The segmentation engine 106 includes a probabilistic tractography engine 108, a deterministic tractography engine 110, and an alignment engine 112. The segmentation engine 106 also includes a database 120 that can include diffusion-weighted (DW) images 114, anatomical images 116, and template images 118. In some implementations, the template images 118 can be Montreal Neurological Institute (MNI) template images. In some implementations, the template images 118 can include templates images from data sets other than the MNI template images. In some implementations, the template images 118 can be generated from an previously taken image of the patient's anatomy. The DW images 114 and the anatomical images 116 can be collectively referred to as imaging data. The system 100 also includes one or more client devices 122. The client devices 122 can communicate with the segmentation engine 106 and the imaging system 102 via the network 104 or other connection.

The system 100 includes the imaging system 102 that provides imaging data to the segmentation engine 106. The imaging system 102 can be one or more magnetic resonance imaging (MRI) systems. The imaging system 102 can be configured to acquire imaging data using different imaging acquisition modalities. The imaging system 102 can be configured to capture and generate both anatomical images 116 and DW images 114. For example, the imaging system 102 can acquire T1, T2, high-angular resolution diffusion images (HARDI), functional Mill (fMRI), magnetization-prepared rapid gradient-echo (MPRAGE), fluid-attenuated inversion recovery (FLAIR), diffusion tensor imaging (DTI), diffusion spectrum imaging (DSI), magnetic resonance spectroscopy or any combination thereof.

In some implementations, a first imaging system 102 can capture and generate the anatomical images 116 and a second imaging system 102 can capture and generate the DW images 114. In some implementations, the imaging system 102 provides the imaging data directly to the segmentation engine 106 through a direct (or local) data or network connection. For example, the imaging system 102 and the segmentation engine 106 can be located in the hospital setting or the segmentation engine 106 can be a component of the imaging system 102 or the system that controls the imaging system 102.

In some implementations, the imaging system 102 can provide the DW images 114 and the anatomical images 116 to the segmentation engine 106 through the network 104, which can be the Internet. A user of the imaging system 102 can upload the DW images 114 and anatomical images 116 to one or more intermediary devices. For example, the imaging system 102 can first provide the imaging data to an intermediary device such as a networked server, cloud based storage, removable storage, or other computer in association with the segmentation engine 106, and the segmentation engine 106 can retrieve the imaging data from the intermediary device prior to the analysis of the imaging data by the segmentation engine 106.

The anatomical images 116 can be T1 weighted, anatomical magnetic resonance (MR) images. The segmentation engine 106 can use the anatomical images 116 to propagate anatomical ROI waypoints from the template images 118 into subject-space. In some implementations, the anatomical images 116 are not gadolinium enhanced. The anatomical images can have an isotropic resolution of between about $1.5 \times 1.5 \times 1.5$ mm$^3$ and about $0.5 \times 0.5 \times 0.5$ mm$^3$. The DW images 114 can be DTI or HARDI images. The segmentation engine 106 can use the DW images 114 to derive 3-dimensional streamline estimates of white matter fiber trajectories and determine locations of fiber bundles or "fascicles." The resolution of the DW images 114 can be between about $1 \times 1 \times 1$ mm$^3$ and about $3 \times 3 \times 3$ mm$^3$. The DW images 114 can be captured between about 20 and about 60 directions or between about 20 and 45 directions.

In some implementations, the segmentation engine 106 can be a component of a cloud platform that can be accessed through a web browser interface. For example, interaction with the segmentation engine 106 may not require the installation of specialist software underpinning neuroimage processing or computational resources at a remote client device 122. The segmentation engine 106 can be accessed through any network-enabled data processing system through a web browser. For example, the client device 122 can be a laptop computer, desktop computer, tablet computer, smart phone, or other computer system that includes one or more processors. The one or more processors can execute a web browser that connects to the segmentation engine 106 and other servers via the network 104.

The segmentation engine 106 can be a component of a data processing system. The segmentation engine 106 can include at least one logic device such as a computing device having a processor to communicate via the network 104, for example, with the imaging system or client device 122. The segmentation engine 106 can include at least one computation resource, server, processor, or memory. For example, the segmentation engine 106 can include a plurality of computation resources or servers located in at least one data center. The segmentation engine 106 can be executed by one or more servers. The one or more servers can include multiple, logically-grouped servers and facilitate distributed computing techniques. The one or more servers can be hosted in a data center, server farm, or a machine farm. The servers can also be geographically dispersed. The one or more servers can be stored in high-density rack systems, along with associated storage systems, and located in an enterprise data center. For example, consolidating the servers in this way may improve system manageability, data security, the physical security of the system, and system performance by locating servers and high performance storage systems on localized high performance networks.

In some implementations, the segmentation engine 106 is a stand-alone device, such as a local computer workstation. The segmentation engine 106 can be a component of another device, such as the imaging system 102. For example, the imaging system 102 can generate the imaging data, and the segmentation engine 106 can then segment the imaging data locally on the imaging system 102. The segmentation engine 106 can include special purpose logic circuitry (e.g., a field programmable gate array (FPGA) or an application specific integrated circuit (ASIC)), a microprocessor, or a combination thereof. The segmentation engine 106 can be coupled with a computer or the imaging system 102 via a wired or wireless network connection or other wired or wireless connections, such as, but not limited to, a universal serial bus (USB) connection, FireWire connection, eSATA connection, or Thunderbolt connection. In some implementations, the segmentation engine 106 can be implemented as a component of another system, such as a desktop computer, and one or more components of the segmentation engine 106 can be implemented as components of the other system.

The segmentation engine 106 can include or otherwise be connected with the database 120. The database 120 can be stored on a computer readable medium such as, but not limited to, a magnetic disk hard drive, random-access memory (RAM), electrically-erasable ROM (EEPROM), erasable-programmable ROM (EPROM), flash memory, optical media, or any other suitable medium for storing the processor executable instructions, the DW images 114, the anatomical images 116, and the template images 118. The database 120 can include a cloud-based data storage system. The cloud-based data storage system can be hosted remote to the segmentation engine 106.

The segmentation engine 106 can store image data, such as the DW images 114 and the anatomical images 116, into the database 120. The anatomical image 116 can include T1 and T2 images. The DW images 114 can include HARDI and other diffusion-weighted images.

The segmentation engine 106 can store one or more template images 118. The template images 118 can include a plurality of MRI generated images that are normalized to provide population-representative MRI images. For example, the template images 118 can be MNI template images that are generated by averaging or otherwise combining a plurality of MRI images. In some implementations, the segmentation engine 106 can store template images from other standard or reference brains. For example, the template images can be from a brain atlas. In some implementations, the template images can be generated based on one or more MRI images of a specific patient.

The segmentation engine 106 can include an alignment engine 112. The alignment engine 112 can be any script, file, program, application, set of instructions, or computer-executable code, that is configured to enable a computing device on which the alignment engine 112 is executed to generate transformations between the template images 118 and the anatomical images 116. The alignment engine 112 can map anatomical images 116 to their respective template images 118 or template images 118 to their respective anatomical images 116. For example, an anatomical image 116, such as a T1 image, can be warped to a template image 118 using a symmetric, invertible warp. Each of the template images 118 can define one or more regions of interest (ROI).

The ROIs can indicate predefined regions, waypoints, anatomical structures, or functional regions. For example, to extract the cortico-spinal tract (CST), the white matter structure connecting the spinal cord with the motor cortex, three ROIs can be used in each hemisphere (separately for each hemisphere). The ROIs can include the pre-central gyms, which can be referred to as the motor cortex. The pre-central gyms can be extracted from the ANTs cortical segmentation and parcellation. The pre-central gyms can be an example of a gray matter ROI. Another example ROI can be the internal capsule in the relevant hemisphere (left or right). The internal capsule is a region of white matter next to the thalamus, through which the midbody of the CST extends. Another example, ROI can be an ROI enclosing the relevant side of the cerebral peduncle (left or right), where the brain-stem extends down towards the spinal cord.

The alignment engine 112 can automatically select the ROIs or the ROIs can be selected through user input. The alignment engine 112 can identify markers present in the template images 118 and the anatomical images 116. When the alignment engine 112 warps the template image 118 onto the anatomical image 116, the alignment engine 112 can generate a mapping between the pixels, voxels, or other points in the template image 118 and the anatomical image 116. For example, the warping can generate a mapping or transformation between the location of the markers identified in the template images 118 and the markers identified in the anatomical images 116. Using the mapping, the alignment engine 112 can map the ROIs from the template image 118 into the anatomical image 116 to enable the ROIs to be localized in the native space of the anatomical image 116.

The alignment engine 112 can map the ROIs from the native space of the anatomical image 116 to the diffusion space of the DW images 114. For example, the ROIs can be mapped to the diffusion space with an affine transformation, such as translation, scaling, homothety, similarity transformation, reflection, rotation, shear mapping, or any combination thereof. The anatomical image can be registered to the diffusion image using global optimisation of a mutual information difference metric. This process can account for the contrast differences between diffusion and anatomical images. The output can be an affine transformation that correctly transforms from the native anatomical space of the patient to the diffusion space such that the ROIs can be co-located with the streamlines in the correct coordinates to extract the fascicles.

The segmentation engine 106 can include a deterministic tractography engine 110 and a probabilistic tractography engine 108. The deterministic tractography engine 110 can be any script, file, program, application, set of instructions, or computer-executable code, that is configured to enable a computing device on which the deterministic tractography engine 110 is executed to deterministically determine tracts within the imaging data. The probabilistic tractography engine 108 can be any script, file, program, application, set of instructions, or computer-executable code, that is configured to enable a computing device on which the probabilistic tractography engine 108 is executed to probabilistically determine tracts within the imaging data.

The segmentation engine 106 can perform multiple tractography passes to automatically identify and segment fibers. For example, the segmentation engine 106 can perform a first pass with deterministic tractography engine 110 and a second pass with the probabilistic tractography engine 108. The segmentation engine 106 can perform multiple passes with the probabilistic tractography engine 108. The segmentation engine 106 can perform multiple passes with the deterministic tractography engine 110.

The deterministic tractography engine 110 can process the DW image 114 to generate streamlines. The streamlines can be virtual representations of white matter fibers in a 3D space. The streamlines can be saved as a data structure that indicates which of the voxels in the DW image 114 are to be included in the streamline. Voxels included in the streamline can include white matter fibers. Each streamline can start at a seed voxel and terminate at a target voxel or target region. The deterministic tractography engine 110 can also generate tractomes, which can be a collection of streamlines from a seed region (e.g., a collection of seed voxels) through the brain imaged in the DW images 114. The deterministic tractography engine 110 can process the DW images 114 with constrained spherical deconvolution techniques to generate a 3D field of directional information that can indicate the direction that follows the axis of the white matter fibers in each region. In some implementations, in the event that low-quality diffusion data is provided, the deterministic tractography engine 110 can use a diffusion tensor model to generate the 3D field of directional information. In some implementations, for relatively high quality diffusion data, the deterministic tractography engine 110 can select from a number of alternative models to generate the 3D field of directional information. For example, the deterministic tractography engine 110 can use the Q-ball model, the Ball and Stick model, the NODDI model, or the multi-tensor model. In some implementations, the deterministic tractography engine 110 can use spherical deconvolution because it is highly capable of robustly resolving complex white matter structure with adequate diffusion data. In some implementations, a b=3000 s/mm$^2$ or b=2000 s/mm$^2$ shell can be used for the constrained spherical deconvolution. From the directional information, the deterministic tractography engine 110 can identify the fibers and streamlines.

The deterministic tractography engine 110 can generate the tracts or streamlines in the 3D space by determining a local diffusion orientation for each voxel in the DW images 114. The deterministic tractography engine 110 can assign a single, local diffusion orientation to each voxel in the DW images 114. Starting with a seed voxel, the deterministic tractography engine 110 can generate a streamline by following the path formed from the local diffusion orientations of voxels. The deterministic tractography engine 110 can generate the streamline with local tractography where the deterministic tractography engine 110 generates the streamline by stepping from voxel to voxel based on the local diffusion orientation of each voxel. The deterministic tractography engine 110 can generate the streamline using global tractography where the streamline is generated based on a fit along the entire pathway from the seed voxel to an end region, such as a ROI, target voxel, or target region.

In some implementations, the deterministic tractography engine 110 can remove some fibers from the tractome. For example, the deterministic tractography engine 110 can select only the streamlines that pass through one or more of the ROIs (or voxels thereof) mapped to the DW images 114. In some implementations, the deterministic tractography engine 110 can select only the streamlines that pass through a plurality of waypoints (e.g., a series of ROIs). Each of the waypoints can be collection of voxels that define, for example, a ROI. For example, the deterministic tractography engine 110 can select the streamlines that pass from a first white matter structure (e.g., a first waypoint) to a second white matter structure (e.g., a second waypoint).

In some implementations, the deterministic tractography engine 110 can refine the ROIs. For example, the initial ROIs (mapped from the template images 118) may be broad ROIs that can cover a volume larger than the patient's actual ROI. The ROI can be defined by a plurality of voxels. The deterministic tractography engine 110 can refine the ROIs by retaining only the voxels of the initial ROIs that are intersected by one or more streamlines. The deterministic tractography engine 110 can save the subset of the voxels from the initial ROIs that are intersected by the one or more streams as refined ROIs.

The segmentation engine 106 can also process the DW images 114 with the probabilistic tractography engine 108. The probabilistic tractography engine 108 can generate additional possible streamlines. Rather than assigning a single, local diffusion orientation to each voxel, the probabilistic tractography engine 108 can assign a probability distribution of orientations to each voxel. The probabilistic tractography engine 108 can generate the possible streamlines from a given seed voxel using a Monte Carlo simulation. The deterministic tractography engine 110 can generate a single streamline from a given seed voxel, and the probabilistic tractography engine 108 can generate a plurality of streamlines from a given seed voxel. The additional possible streamlines can cover a greater volume when compared to the volume covered by the streamlines identified by the deterministic tractography engine 110. The probabilistic tractography engine 108 can filter the probabilistically determined streamlines with the refined ROIs to generate a final set of streamlines. For example, the probabilistic tractography engine 108 can discard streamlines that do not pass through the refined ROIs. In some implementations, the segmentation engine 106 can generate a plurality of refined ROIs as waypoints along a pathway. The probabilistic tractography engine 108 can discard streamlines that do not pass through each of the refined ROIs along the pathway. In some implementations, the probabilistic tractography engine 108 can discard streamlines that do not pass through a predefined percent (e.g., 90%) of the refined ROIs along the pathway.

In some implementations, the probabilistic tractography engine 108 can account for errors or shortcomings of the deterministic tractography engine's tractography determination. For example, the deterministic tractography engine 110 can generate errors as the streamline is propagated from voxel to voxel. For example, the deterministic tractography engine 110 can use information derived from the DW images 114 by first fitting a model in each voxel of the DW images 114. The model can provide the likely directions of WM fibers traversing each of the voxels. From a starting location (e.g., a seed point or seed voxel), the deterministic tractography engine 110 can generate a streamline from the starting location by following the most likely direction at each voxel.

In some implementations, the resolution of the DW images 114 can be between about 1 mm and about 3 mm. In the volume of each voxel, white matter fibers can curve, bifurcate, diverge, or cross other fibers. In some implementations, the deterministic tractography engine 110 can generate less accurate direction predictions for voxels where the fiber might curve, bifurcate, diverge, or cross another fiber because within these voxels diffusion does not substantially occur in a single direction.

To account for voxels where the deterministic tractography engine 110 can generate less accurate direction predictions, the probabilistic tractography engine 108 can fit a distribution of potential fiber directions to each voxel. The probabilistic tractography engine 108 can run a Monte Carlo simulation to test potential pathways based on the distribution of potential fiber directions for each voxel. The probabilistic tractography engine 108 can run 100s, 1000s, or 10000s of Monte Carlo simulations to generate potential pathways. From the Monte Carlo simulations, the probabilistic tractography engine 108 can generate a distribution of candidate pathways (or streamlines). As discussed above, the distribution of candidate pathways can be filtered with refined ROIs to generate a final set of streamlines.

Figure 2:
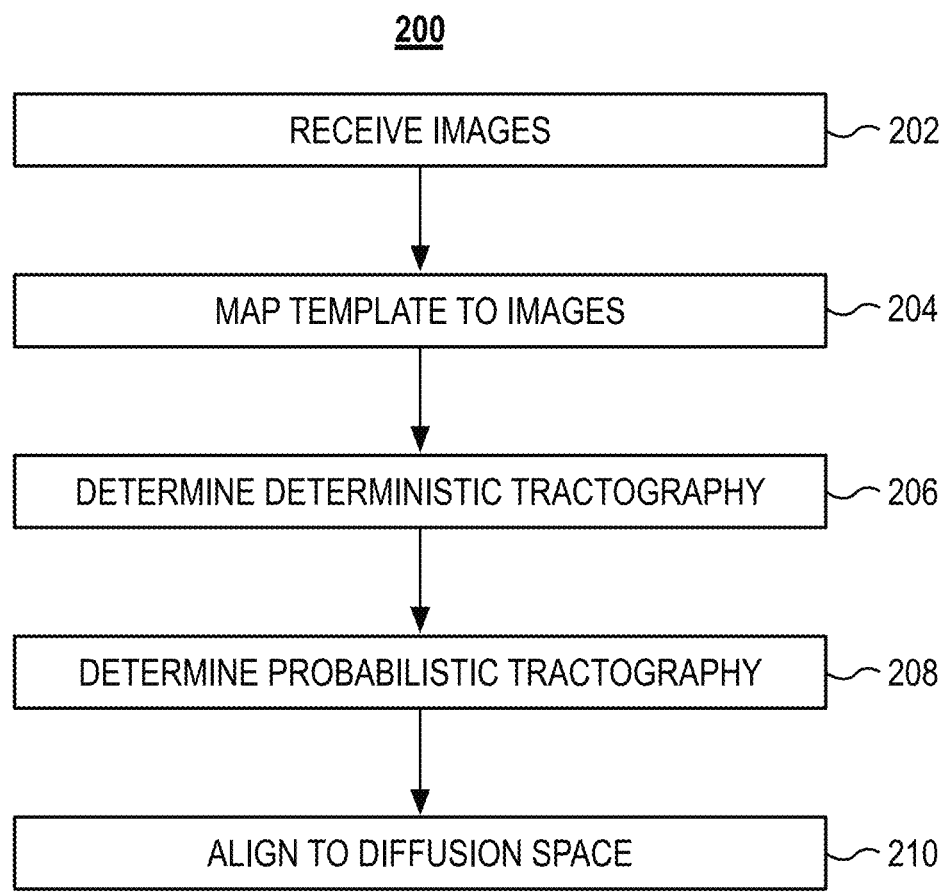
FIG. 2 illustrates a block diagram of an example method for tract segmentation.

FIG. 2 illustrates a block diagram of an example method 200 for tract segmentation. The method 200 can include receiving images (BLOCK 202). The method 200 can include mapping templates to the images (BLOCK 204). The method 200 can include determining a deterministic tractography (BLOCK 206). The method 200 can include determining a probabilistic tractography (BLOCK 208). The method 200 can include aligning the tractography to the diffusion space (BLOCK 210).

As set forth above, the method 200 can include receiving images (BLOCK 202). Also referring to FIG. 1, the images can be image data that is received from the imaging system 102. The image data can include DW images 114 and anatomical images 116. The segmentation engine 106 can receive the image data from a single imaging system 102 or from multiple imaging systems 102. In some implementations, a user can upload the image data to the segmentation engine 106 via a network 104, such as the internet.

The method 200 can include mapping templates to the image (BLOCK 204). The segmentation engine 106 can store the templates in the form of template images 118. The templates can be an anatomical atlas or other form of normalized anatomical images. In some implementations, the templates can include ROIs. The ROIs can indicate predefined regions, waypoints, anatomical structures, or functional regions. The alignment engine 112 can map the template to the received image data, such as the anatomical image 116 and the DW images 114. The alignment engine 112 can calculate a correspondence between the template and the image data that enables the ROIs to be mapped to the image data.

The method 200 can include a deterministic tractography (BLOCK 206). The deterministic tractography engine 110 can process the DW images 114 to generate streamlines. The deterministic tractography engine 110 can process the DW images 114 with constrained spherical deconvolution techniques to generate a 3D field of directional information that can indicate the direction that follows the axis of the white matter fibers in each region. From the directional information, the deterministic tractography engine 110 can identify the fibers and streamlines by following the directions from a seed location.

In some implementations, the deterministic tractography engine 110 can filter the identified streamlines by determining which of the streamlines pass through one or more predetermined ROIs. In some implementations, the deterministic tractography engine 110 can refine the ROIs.

Figure 3B:
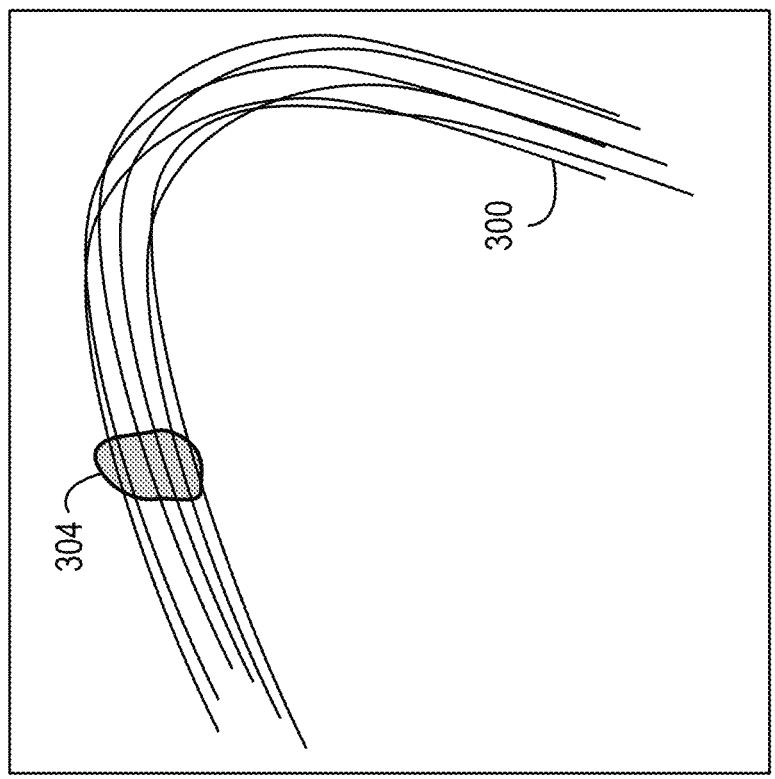
FIGS. 3A and 3B illustrate the refinement of the regions of interest.
Figure 3A:
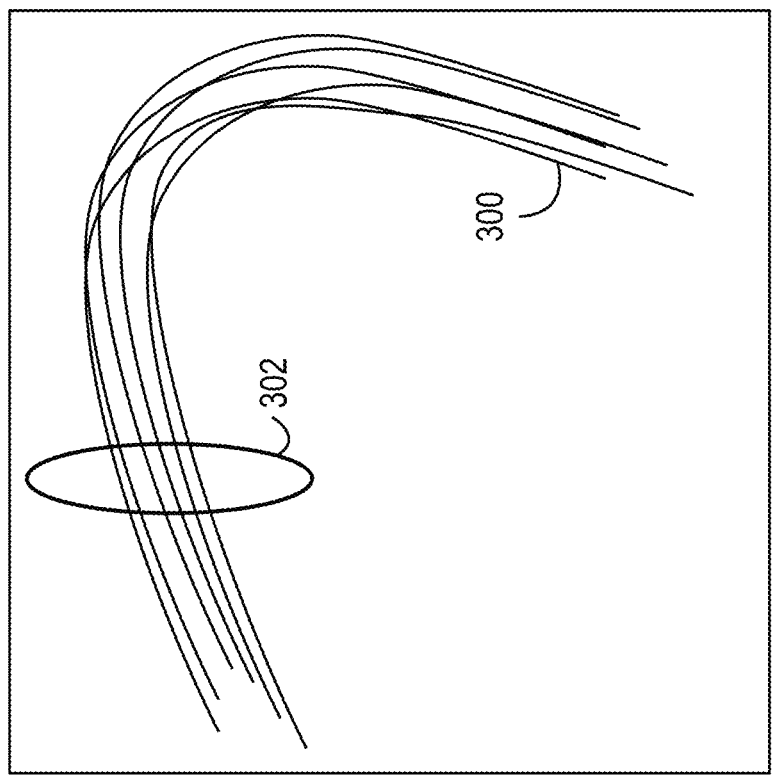

FIGS. 3A and 3B illustrate an example refinement of the ROIs. FIG. 3A illustrates a plurality of streamlines 300 that pass through an ROI 302. The ROI 302 can include a plurality of voxels. The deterministic tractography engine 110 can determine which of the ROI's voxels the streamlines 300 pass through. FIG. 3B illustrates the plurality of streamlines 300 that pass through the refined ROI 304. The deterministic tractography engine 110 can generate the refined ROI 304 as the subset or portion of voxels from the ROI 302 through which a streamline 300 passed.

Referring to FIG. 2, the method 200 can include determining a probabilistic tractography (BLOCK 208). As discussed above, deterministic tractography can generate errors caused by intra-voxel curves, bifurcations, or fiber crossings. For each voxel, the probabilistic tractography engine 108 can generate a distribution of potential fiber directions. The probabilistic tractography engine 108 can run Monte Carlo simulations that incorporate the possible fiber directions to generate a distribution of candidate pathways. The probabilistic tractography engine 108 can prune the candidate pathways by applying the refined ROIs to the candidate pathways. For example, candidate pathways that do not pass through the refined ROIs can be discarded.

Figure 4A:
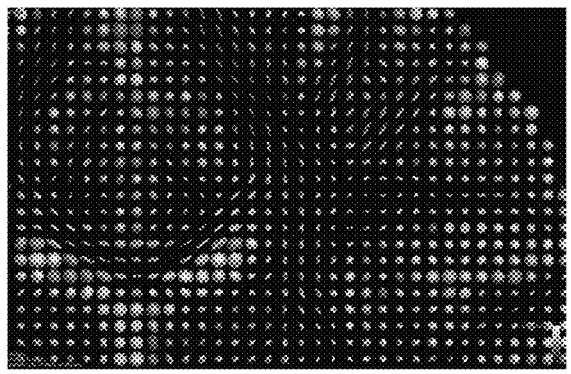
FIG. 4A illustrates an example voxel-wise model of standard diffusion tensor tractography.
Figure 4B:
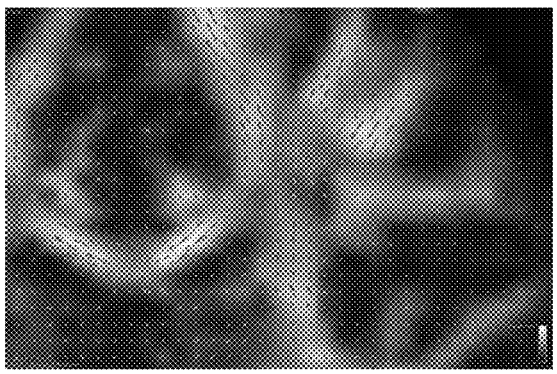
FIG. 4B illustrates a tractography calculation using constrained spherical deconvolution.

FIG. 4A illustrates an example voxel-wise model 400 of standard diffusion tensor tractography. The standard diffusion tensor tractography image illustrates that the standard diffusion tensor tractography fails to capture fiber crossings. FIG. 4B illustrates a tractography calculation 402 using constrained spherical deconvolution, which is better able to capture crossing fiber structures.

Figure 4C:
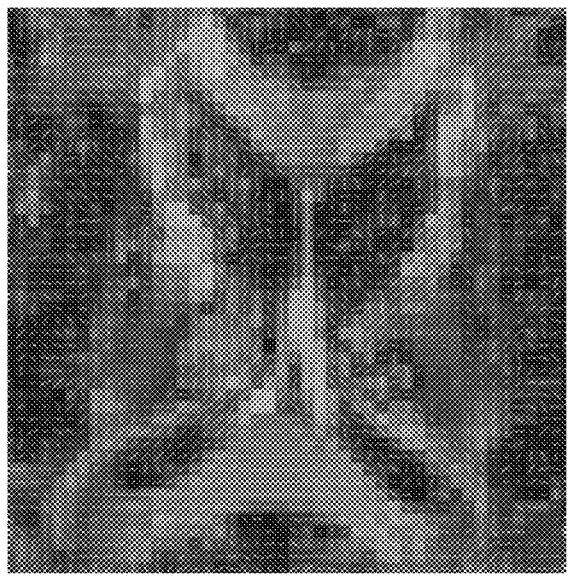
FIG. 4C illustrates a voxel-wise model of standard diffusion tensor tractography.
Figure 4D:
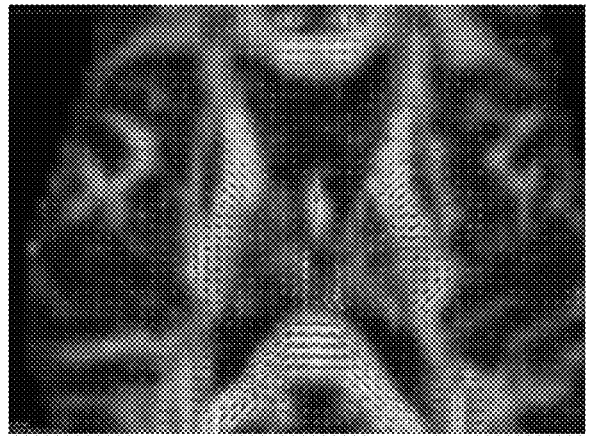
FIG. 4D illustrates a probabilistic tractography model.

FIG. 4C illustrates a voxel-wise model 404 of standard diffusion tensor tractography. As illustrated in FIG. 4C, each voxel is assigned a single fiber direction. FIG. 4D illustrates a probabilistic tractography model 406. Each voxel is assigned a distribution of potential fiber directions, which better captures curvature, dispersion, and fiber crossings.

Figure 5B:
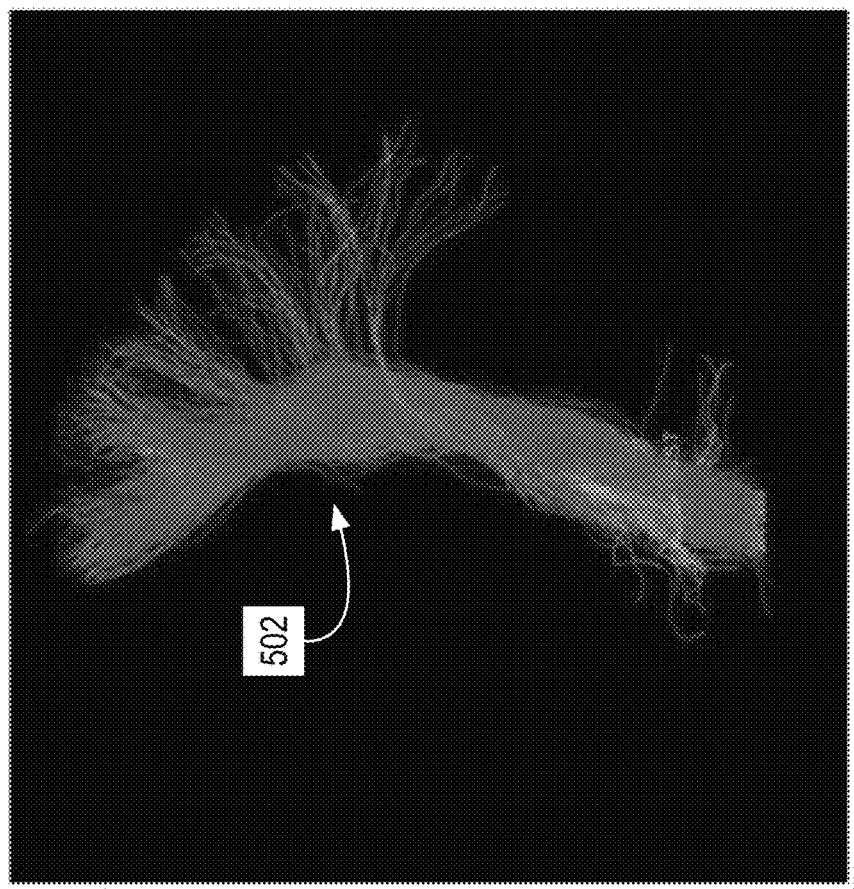
FIG. 5B illustrates the pyramidal tract segmented using a combination of deterministic and probabilistic tractography.
Figure 5A:
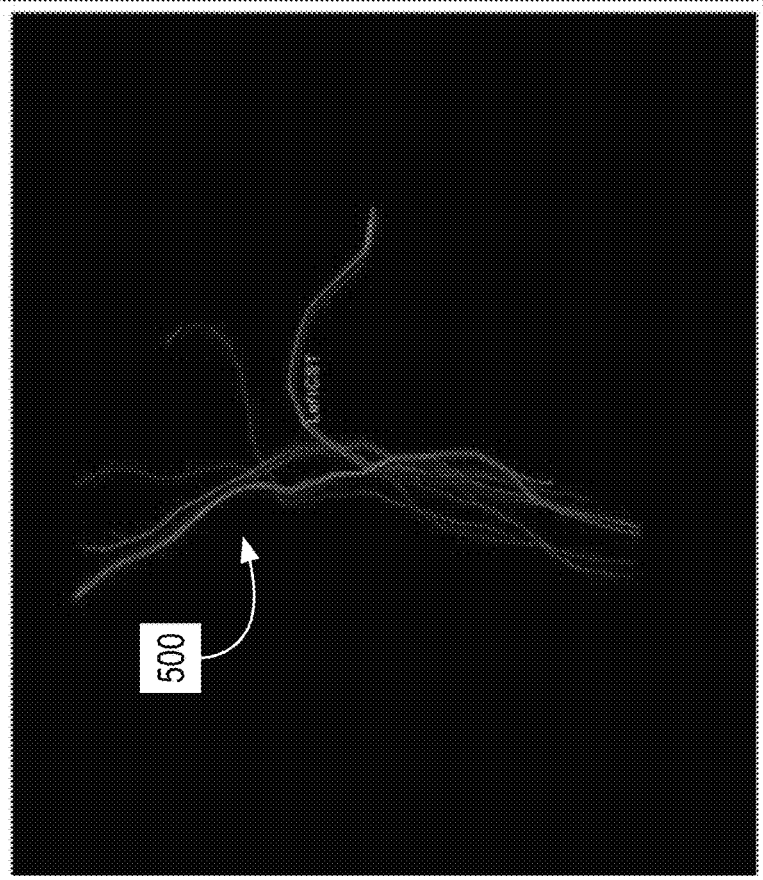
FIG. 5A illustrates a pyramidal tract segmented using only deterministic tractography.

FIG. 5A illustrates a pyramidal tract 500 segmented using only deterministic tractography. FIG. 5B illustrates the pyramidal tract 502 segmented using a combination of deterministic and probabilistic tractography. As illustrated, the pyramidal tract that was generated through the method described herein using both deterministic and probabilistic tractography covers a greater amount of the pyramidal structure.

Figure 6:
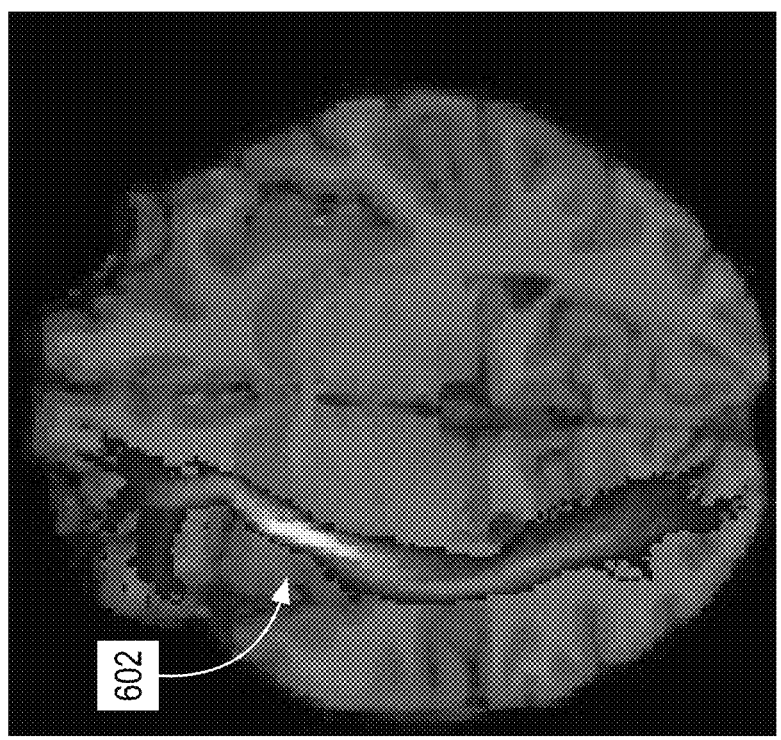
FIG. 6 illustrates the overlay of the segmented tract profile over the anatomical image.

Referring to FIG. 2, the method 200 can include aligning the segmented tract to the diffusion space (BLOCK 210). FIG. 6 illustrates a DW MRI image 600. The segmented tract 602 is mapped into the diffusion space of the DW MRI image 600. In some implementations, the segmented tract can be aligned or otherwise mapped back to one or more of the DW images 114. In some implementations, the segmented tract can be mapped to one or more of the anatomical images 116. Mapping the segmented tract to the DW images 114 can enable a user to visualize the segmented tract within the patient's anatomy.

Figure 7:
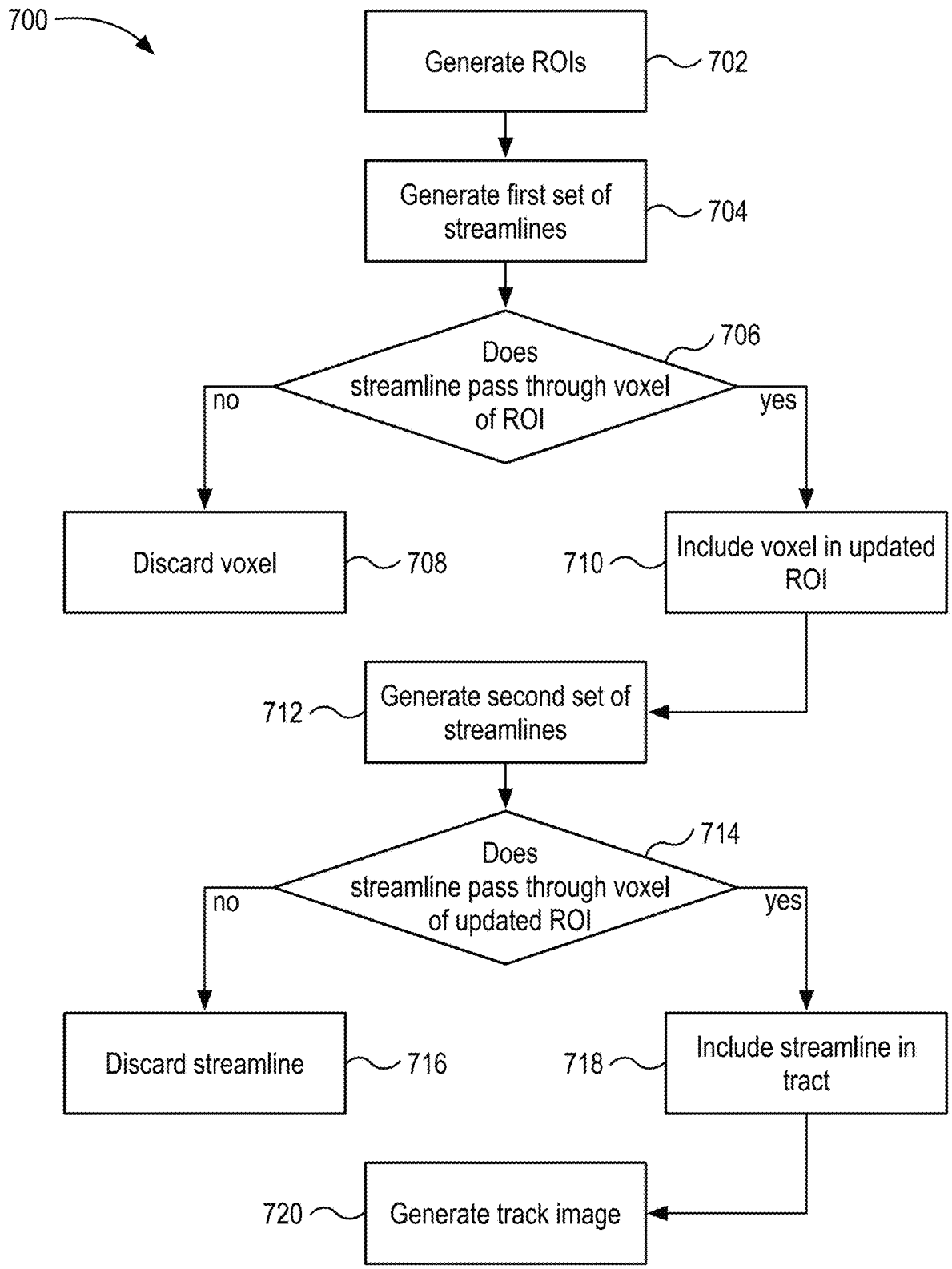
FIG. 7 illustrates a block diagram of an example method for segmenting imaging data using the system illustrated in FIG. 1.

FIG. 7 illustrates a block diagram of an example method 700 for segmenting imaging data. The method 700 can include generating ROIs (BLOCK 702). Also referring to FIG. 1, the segmentation engine 106 can receive image data from the imaging system 102. The image data can include DW images 114 and anatomical images 116. The segmentation engine 106 can receive the image data from a single imaging system 102 or from multiple imaging systems 102. In some implementations, a user can upload the image data to the segmentation engine 106 via a network 104, such as the internet. The segmentation engine 106 can store templates in the form of template images 118 in the database 120. The template images 118 can be an anatomical atlas or other forms of normalized anatomical images (e.g., anatomical images that can include the average of a plurality of anatomical images from different subjects). The template images 118 can include ROIs. As the template images 118 can include normalized anatomical images, the ROIs within the template images 118 can also be normalized or averaged. The normalized ROIs may not correspond to a specific patient or subject but indicate the average location of the ROI from a population of patients or subjects. The ROIs can indicate predefined regions, waypoints, anatomical structures, or functional regions. The alignment engine 112 can map the template images 118 to the received image data, such as the anatomical image 116 and the DW images 114. The alignment engine 112 can calculate a correspondence between the template and the image data that enables the ROIs to be mapped to the image data.

The method 700 can include generating a first set of streamlines (BLOCK 704). In some implementations, the deterministic tractography engine 110 can determine the first set of streamlines. For example, the deterministic tractography engine 110 can process the DW images 114 to generate streamlines. The deterministic tractography engine 110 can process the DW images 114 with constrained spherical deconvolution techniques to generate a 3D field of directional information for each voxel. The directional information can indicate a direction that follows the axis of the white matter fibers through the voxel. Starting from a seed voxel within a seed region, the deterministic tractography engine 110 can generate a streamline by following the direction from the seed voxel to a neighboring voxel. The deterministic tractography engine 110 can repeat the process in a step by step processing following each voxel to a neighboring voxel based on the directional information of the voxel. In some implementations, the deterministic tractography engine 110 can discard any streamlines that do not terminate in or pass through a target region.

The method 700 can generating updated ROIs by determining whether one or more of the streamlines from the first set of streamlines passes through a voxel of the ROI generated at BLOCK 702 (BLOCK 706). For example, the segmentation engine 106 can iterate through each voxel included within the ROI. If the segmentation engine 106 determines that one or more of the streamlines from the first set of streams does not pass through the current voxel, the segmentation engine 106 can discard the current voxel as belonging to the updated ROI (BLOCK 708). If the segmentation engine 106 determines that one or more of the streamlines from the first set of streams does pass through the current voxel, the segmentation engine 106 can include the current voxel in the updated ROI (BLOCK 710). For example, and also referring to FIGS. 3A and 3B, the original ROI 302 can include a plurality of voxels. The segmentation engine 106 can generate an updated or refined ROI 304 that includes a subset of the voxels from the original ROI 302. The segmentation engine 106 can determine whether one or more of the streamlines passes through a voxel of the ROI 302 by generating a data structure, such as an array, that includes a list indicating the voxels contained in the ROI 302. The deterministic tractography engine 110 can generate a data structure for each streamline that indicates through which voxels the streamline passes. The segmentation engine 106 can iterate through each value indicating a voxel contained in the ROI 302 to determine if the value is present in one or more of the streamline data structures.

The method 700 can include generating a second set of streamlines (BLOCK 712). The probabilistic tractography engine 108 can generate the second set of streamlines. For example, for each voxel, the probabilistic tractography engine 108 can generate a distribution of potential fiber directions. The probabilistic tractography engine 108 can run Monte Carlo simulations that incorporate the possible fiber directions to generate a distribution of candidate pathways. For example, for each seed voxel, the probabilistic tractography engine 108 can generate a plurality of streamlines. The probabilistic tractography engine 108 can generate the second set of streamlines as the plurality of streamlines starting from each of a plurality of seed voxels within a seed region. The second set of streamlines can be referred to as candidate pathways or candidate streamlines.

The method 700 can determine whether the streamlines of the second set of streamlines pass through the updated ROIs (BLOCK 714). The segmentation engine 106 can use the updated ROIs, generated at BLOCK 710, to prune the second set of streamlines. The segmentation engine 106 can prune a streamline from the second set of streamlines if the streamline does not pass through the updated ROI. The segmentation engine 106 can prune a streamline from the second set of streamlines if the streamline does not pass through each of a plurality of updated ROIs along a predetermined pathway. The segmentation engine 106 can prune a streamline from the second set of streamlines if the streamline does not pass through a predetermined number of the plurality of updated ROIs along a predetermined pathway.

Figure 8:
FIG. 8 illustrates a first view and a second view of an example tract image generated with system illustrated in FIG. 1.

The method 700 can include generating a tract image (BLOCK 720). In some implementations, the tract image can include just the pruned second set of streamlines, as illustrated in FIG. 5B. In some implementations, the tract image can include anatomical data. For example, the streamlines can be mapped to DW images 114 or anatomical images 116. For example, the segmentation engine 106 can generate the tract image by aligning the pruned second set of streamlines to the diffusion space of the DW MRI images. In some implementations, the segmented tract can be mapped to one or more of the anatomical images 116. Mapping the segmented tract to the DW images 114 can enable a user to visualize the segmented tract within the patient's anatomy. The tract image can be a probabilistic fiber probability map that is derived from voxel fiber-count maps of the pruned second set of streamlines. The pruned second set of streamlines can be fascicles, such as the fornix, left and right; the forceps major; the forceps minor; the corticospinal tract (CST), left and right; the inferior fronto-occipital fasciculus (IFOF), left and right; the inferior longitudinal fasciculus (ILF); the uncinate fasciculus (UNC); the superior longitudinal fasciculus (SLF); the cingulum, left and right; or any combination thereof. FIG. 8 illustrates a first view 800 and a second view 802 of an example tract image. Each image includes a plurality of fascicles 804.

In some implementations, the segmentation engine 106 can calculate one or more metrics of the segmented tract. The metrics can be a quantification of mean scalar metric for the segmented tract or fascicle. The scalar metrics can include fractional anisotropy (FA), mean diffusivity (MD), radial diffusivity (RD), axial diffusivity (AD), coefficient of planarity (Cp), coefficient of sphericity (Cs), coefficient of linearity (Cl), or any combination thereof.

In some implementations, the segmentation engine 106 can calculate or determine a probabilistic map of voxel-fiber membership. The probabilistic map of voxel-fiber membership gives a number for each voxel that is proportional to the number of streamlines crossing that voxel. For a voxel that is intersected by many streamlines estimated to be members of the candidate fascicle, this number is high, whereas, in any voxel intersected by very few streamlines estimated to be members of the candidate fascicle this number will be low. In some implementations, the voxel can be retained as a member of the candidate fascicle if the number is above a predetermined threshold. The weighted statistics described herein can be calculated using the voxel-fiber membership value using the equation:

$$\bar{f} = \frac{\sum_i v_i f_i}{\sum_i v_i}$$

The above equation provides the weight mean $\bar{f}$ of the scalar metric. In the equation, $v_i$ is the value of the probabilistic map of fiber membership in voxel i. The term $v_i$ is proportional to the number of reconstructed streamlines estimated to be part of the candidate fascicle intersecting voxel i. In the equation, $f_i$ is the value of the scalar metric in voxel i, e.g. fractional anisotropy (FA), mean/radial/axial diffusivity (MD, RD, MD), or coefficient of linearity/planarity/sphericity (Cl, Cl, Cs).

Figure 9:
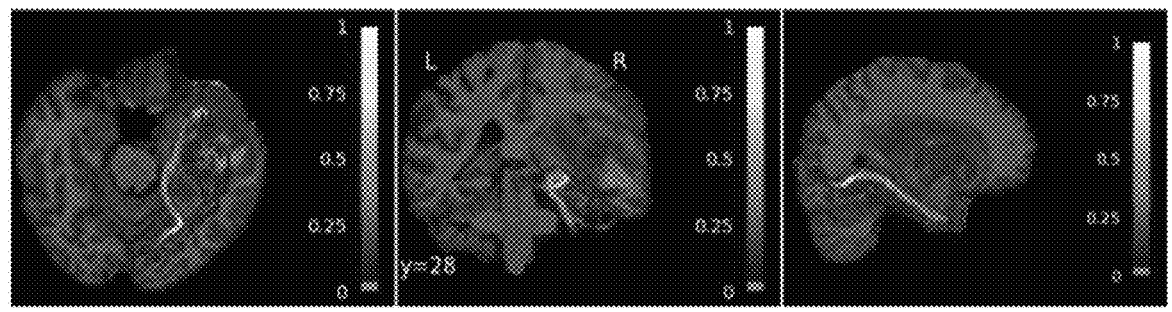
FIG. 9 illustrates an example tract image that includes multiple images each with a different tract generated with system illustrated in FIG. 1.
Figure 9:
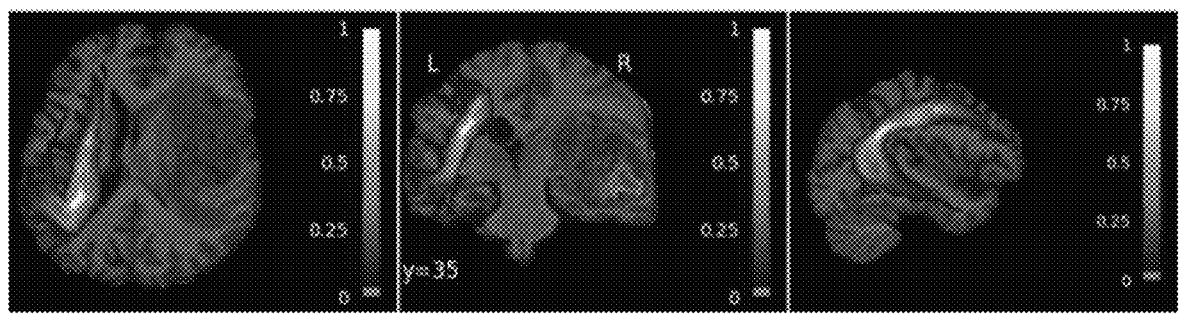
Figure 9:
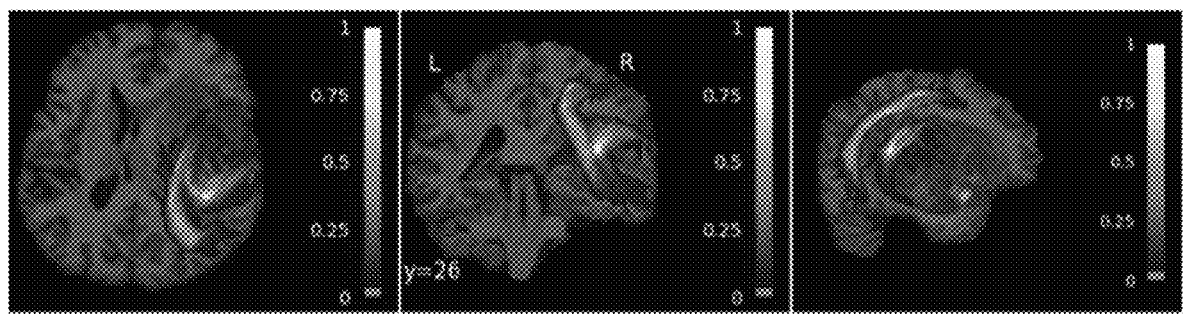
Figure 9:
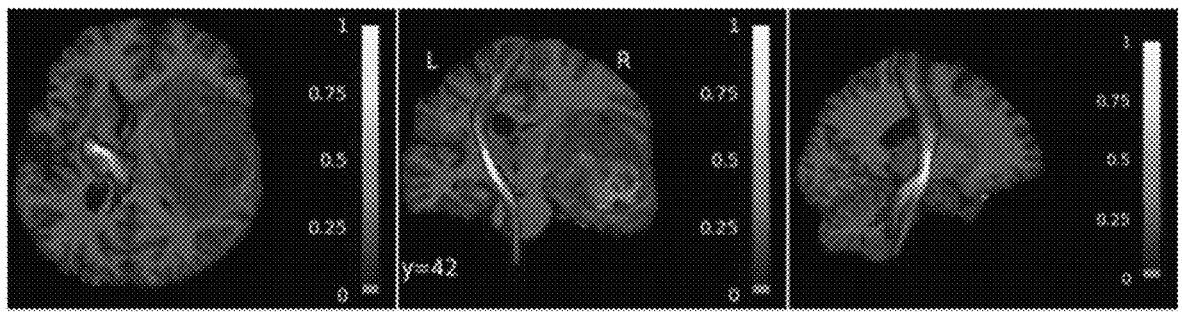

In some implementations, the tract image can include multiple images. For example, each image can include a different tract. FIG. 9 illustrates an example tract image 900 that includes multiple images each with a different tract. For example, each image within a given row illustrates the same tract viewed from three different planar projections. The tracts can be displayed as a probability membership map that indicates the probability that each streamline is a member of the tract or fascicle. The tract image can also include a table with each of the scalar diffusion metrics near each image.

Figure 10:
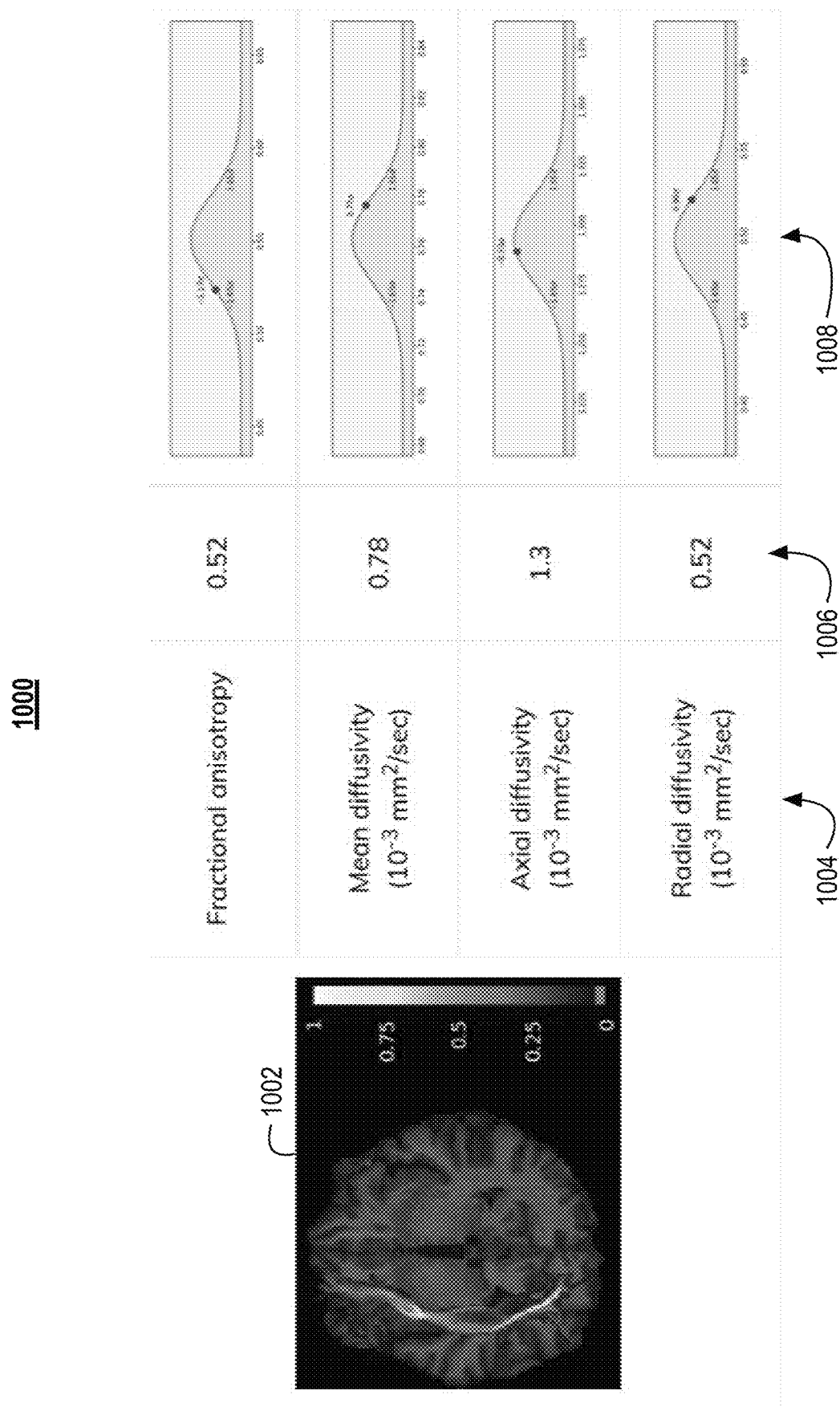
FIGS. 10 and 11 illustrate example tract images generated with system illustrated in FIG. 1.
Figure 11:
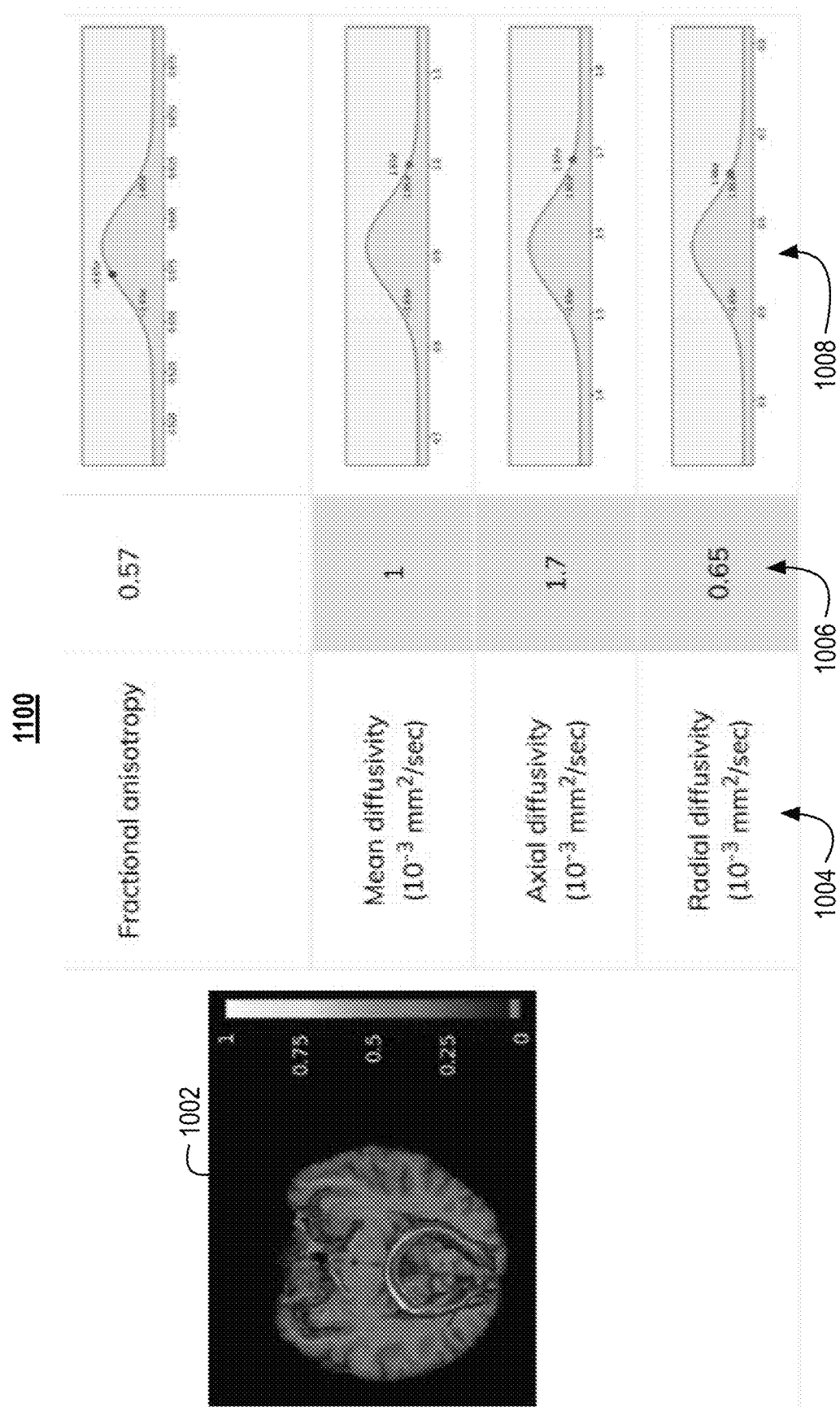

In some implementations, the tract image can include indications of whether the calculated metrics are within predetermined, normal distributions. For example, FIG. 10 illustrates an example tract image 1000. The tract image 1000 includes an image 1002 including the left inferior fronto-occipital fasciculus. The tract image 1000 can include a table listing a plurality of metrics 1004 with their corresponding values 1006. The tract image 1000 can include distributions 1008 that indicate whether the corresponding values 1006 are within a normal distribution. As illustrated in FIG. 10, the subject is a health subject and each of the metrics are within the normal distribution. FIG. 11 illustrates a tract image 1100 similar to tract image 1000. The tract image 1100 is from a subject that experience traumatic brain injury. As illustrated in FIG. 11, two of the metrics distributions 1008 are outside the normal distribution indicating trauma to the subject's brain.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including," "comprising," "having," "containing," "involving," "characterized by," "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed:

1. A data processing system comprising one or more processors to segment neurological tracts, the data processing system configured to:
   generate, based on a diffusion-weighted (DW) image of image data, a first plurality of streamlines indicating a fiber tract in the DW image;
   select a subset of a first plurality of voxels associated with an anatomical image of the image data based on at least one of the first plurality of streamlines passing through each voxel of the subset of the first plurality of voxels, wherein the subset of the first plurality of voxels is associated with a region of the anatomical image;
   generate a second plurality of streamlines, each of the second plurality of streamlines indicating a candidate fiber tract;
   select a subset of the second plurality of streamlines, each streamline of the subset of the second plurality of streamlines passes through the region of the anatomical image; and
   generate a tract image comprising the subset of the second plurality of streamlines, wherein each streamline of the subset of the second plurality of streamlines passes through the region of the anatomical image.

2. The data processing system of claim 1, wherein the data processing system generates the first plurality of streamlines indicating the fiber tract with deterministic tractography.

3. The data processing system of claim 1, wherein the data processing system generates the second plurality of streamlines with probabilistic tractography.

4. The data processing system of claim 1, wherein the region is a part of a plurality of regions of the anatomical image, and wherein the data processing system maps the plurality of regions from a template to the anatomical image.

5. The data processing system of claim 4, wherein the template comprises a Montreal Neurological Institute (MNI) template image.

6. The data processing system of claim 4, wherein the data processing system warps the template to the anatomical image with a symmetric, invertible warp.

7. The data processing system of claim 1, wherein the data processing system generates the first plurality of streamlines using constrained spherical deconvolution.

8. The data processing system of claim 1, wherein the tract image comprises the subset of the second plurality of streamlines aligned with the anatomical image.

9. The data processing system of claim 1, wherein the anatomical image is an MRI image.

10. The data processing system of claim 1, wherein the data processing system is configured to:
    select a subset of a second plurality of voxels associated with the anatomical image of the image data based on at least one of the first plurality of streamlines passing through each voxel of the subset of the second plurality of voxels, wherein the subset of the second plurality of voxels is associated with a second region of the anatomical image; and
    select the subset of the second plurality of streamlines, wherein each streamline of the subset of the second plurality of streamlines passes through the second region.

11. A method to segment neurological tracts, comprising:
    generating, by a segmentation engine, based on a diffusion-weighted (DW) image of image data, a first plurality of streamlines indicating a fiber tract in the DW image;
    selecting, by the segmentation engine, a subset of a first plurality of voxels associated with an anatomical image of the image data based on at least one of the first plurality of streamlines passing through each voxel of the subset of the first plurality of voxels, wherein the subset of the first plurality of voxels is associated with a region of the anatomical image,
    generating, by the segmentation engine, a second plurality of streamlines, each of the second plurality of streamlines indicating a candidate fiber tract;
    selecting, by the segmentation engine, a subset of the second plurality of streamlines, each streamline of the subset of the second plurality of streamlines passes through the region of the anatomical image; and
    generating, by the segmentation engine, a tract image comprising the subset of the second plurality of streamlines, wherein each streamline of the subset of the second plurality of streamlines passes through the region of the anatomical image.

12. The method of claim 11, further comprising generating the first plurality of streamlines indicating the fiber tract with deterministic tractography.

13. The method of claim 11, further comprising generating the second plurality of streamlines with probabilistic tractography.

14. The method of claim 11, wherein the region is a part of a plurality of regions of the anatomical image, further comprising mapping the plurality of regions from a template to the anatomical image.

15. The method of claim 14, wherein the template comprises a Montreal Neurological Institute (MNI) template image.

16. The method of claim 14, further comprising warping the template to the anatomical image with a symmetric, invertible warp.

17. The method of claim 11, further comprising generating the first plurality of streamlines using constrained spherical deconvolution.

18. The method of claim 11, wherein the tract image comprises the subset of the second plurality of streamlines aligned with the anatomical image.

19. The method of claim 11, wherein the anatomical image is an MRI image.

20. The method of claim 11, further comprising:
- selecting, by the segmentation engine, a subset of a second plurality of voxels associated with the anatomical image of the image data based on at least one of the first plurality of streamlines passing through each voxel of the subset of the second plurality of voxels, wherein the subset of the second plurality of voxels is associated with a second region of the anatomical image; and
- selecting, by the segmentation engine, the subset of the second plurality of streamlines, wherein each streamline of the subset of the second plurality of streamlines passes through the second region.

* * * * *